US011782967B2

(12) United States Patent
Erpenbach et al.

(10) Patent No.: US 11,782,967 B2
(45) Date of Patent: *Oct. 10, 2023

(54) DETERMINING USER INTERACTIONS WITH NATURAL LANGUAGE PROCESSOR (NPL) ITEMS IN DOCUMENTS TO DETERMINE PRIORITIES TO PRESENT NPL ITEMS IN DOCUMENTS TO REVIEW

(71) Applicant: International Business Machines Corporation, Armonk, NY (US)

(72) Inventors: Eric L. Erpenbach, Oronoco, MN (US); Andrew J. Lavery, Austin, TX (US); Richard J. Stevens, Monkton, VT (US); Fernando J. Suarez Saiz, Armonk, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 769 days.

This patent is subject to a terminal disclaimer.

(21) Appl. No.: 15/811,225

(22) Filed: Nov. 13, 2017

(65) Prior Publication Data

US 2019/0147055 A1 May 16, 2019

(51) Int. Cl.
*G06F 16/435* (2019.01)
*G06F 16/93* (2019.01)
(Continued)

(52) U.S. Cl.
CPC .......... *G06F 16/435* (2019.01); *G06F 16/93* (2019.01); *G06F 40/10* (2020.01); *G06F 40/284* (2020.01); *G16H 10/60* (2018.01); *G06F 16/182* (2019.01)

(58) Field of Classification Search
CPC ...... G06F 16/435; G06F 16/93; G06F 16/182; G16H 10/60
(Continued)

(56) References Cited

U.S. PATENT DOCUMENTS 5,493,677 A    2/1996  Balogh et al.
8,095,544 B2 * 1/2012  Boone ................... G16Z 99/00
                                            707/750
(Continued)

OTHER PUBLICATIONS

Chapman et al., "What can natural language processing do for clinical decision support?", 2009, Journal of Biomedical Informatics, pp. 760-772, 13 pages printed. (Year: 2009).*
(Continued)

*Primary Examiner* — Tony Mahmoudi
*Assistant Examiner* — Michael Le
(74) *Attorney, Agent, or Firm* — KONRAD RAYNES DAVDA & VICTOR LLP; David W. Victor

(57) ABSTRACT

Provided are a computer program product, system, and method for determining user interactions with natural language processor (NLP) items in documents to determine priorities to present NLP items in documents to review. Information is received on user interactions with natural language processing (NLP) items in documents presented at least one computing device. Indication is made in a database of user interaction information on the user interactions with the NLP items indicated in the received transmitted information. The user interaction information in the database providing interaction information for NLP items in the selected document is used to determine an order of the NLP items in the selected document. Content of the NLP items in the selected document is transmitted to present to a reviewing user at a reviewing computing device in the determined order.

20 Claims, 8 Drawing Sheets

(51) Int. Cl.
*G06F 16/182* (2019.01)
*G16H 10/60* (2018.01)
*G06F 40/10* (2020.01)
*G06F 40/284* (2020.01)

(58) Field of Classification Search
USPC .......................................................... 707/608
See application file for complete search history.

(56) References Cited

U.S. PATENT DOCUMENTS

| | | | |
|---|---|---|---|
| 9,015,185 B2 | 4/2015 | Kanigsberg et al. | |
| 9,282,162 B2 | 3/2016 | Boyle et al. | |
| 9,348,815 B1 | 5/2016 | Estes et al. | |
| 9,535,894 B2 | 1/2017 | Carrier et al. | |
| 10,296,187 B1* | 5/2019 | Gregg | G06F 16/284 |
| 10,395,772 B1* | 8/2019 | Lucas | G16H 10/60 |
| 11,568,964 B2* | 1/2023 | Gupta | G16H 15/00 |
| 2005/0289124 A1* | 12/2005 | Kaiser | G06F 16/24522 |
| 2007/0265831 A1* | 11/2007 | Dinur | G06F 40/232 |
| | | | 704/10 |
| 2007/0299652 A1 | 12/2007 | Koll et al. | |
| 2007/0299664 A1* | 12/2007 | Peters | G06F 40/16 |
| | | | 704/235 |
| 2008/0270120 A1* | 10/2008 | Pestian | G06F 40/20 |
| | | | 704/9 |
| 2009/0306962 A1* | 12/2009 | Harlow | G06F 40/284 |
| | | | 704/9 |
| 2010/0114598 A1* | 5/2010 | Oez | G06Q 10/10 |
| | | | 705/2 |
| 2010/0114600 A1 | 5/2010 | Carosso et al. | |
| 2012/0095862 A1* | 4/2012 | Schiff | G06Q 30/0282 |
| | | | 705/26.7 |
| 2012/0167007 A1* | 6/2012 | Ross | G06Q 10/10 |
| | | | 715/811 |
| 2012/0246081 A1* | 9/2012 | Brown | G06Q 10/10 |
| | | | 705/304 |
| 2012/0246578 A1* | 9/2012 | Baldwin | G06F 3/048 |
| | | | 715/753 |
| 2013/0024382 A1* | 1/2013 | Dala | G06F 21/6245 |
| | | | 705/51 |
| 2013/0054512 A1* | 2/2013 | Ephrat | G16H 40/67 |
| | | | 707/602 |
| 2013/0124964 A1* | 5/2013 | Viegas | G06F 40/295 |
| | | | 715/230 |
| 2013/0191161 A1* | 7/2013 | Churchwell | G16H 10/60 |
| | | | 705/3 |
| 2013/0219257 A1* | 8/2013 | Carmeli | G06F 40/166 |
| | | | 715/226 |
| 2013/0268260 A1 | 10/2013 | Lundberg et al. | |
| 2013/0339030 A1* | 12/2013 | Ehsani | G10L 17/00 |
| | | | 704/275 |
| 2014/0304264 A1* | 10/2014 | Hailpern | G06F 16/35 |
| | | | 707/737 |
| 2014/0337044 A1* | 11/2014 | Heinze | G06Q 10/10 |
| | | | 705/2 |
| 2014/0350954 A1* | 11/2014 | Ellis | G16H 10/60 |
| | | | 705/2 |
| 2014/0358964 A1* | 12/2014 | Woods | G06F 16/3329 |
| | | | 707/769 |
| 2014/0365242 A1* | 12/2014 | Neff | G16H 10/60 |
| | | | 705/3 |
| 2015/0066539 A1* | 3/2015 | Sheffer | G16H 50/20 |
| | | | 705/3 |
| 2015/0127325 A1 | 5/2015 | Birnbaum et al. | |
| 2015/0154174 A1 | 6/2015 | Hoover et al. | |
| 2015/0193583 A1* | 7/2015 | McNair | G16H 50/20 |
| | | | 705/2 |
| 2015/0294089 A1* | 10/2015 | Nichols | G06F 3/0304 |
| | | | 705/3 |
| 2016/0012186 A1* | 1/2016 | Zasowski | G06Q 50/22 |
| | | | 705/3 |
| 2016/0048500 A1 | 2/2016 | Hebert | |
| 2016/0071432 A1* | 3/2016 | Kurowski | G16H 20/30 |
| | | | 434/236 |
| 2016/0098393 A1 | 4/2016 | Hebert | |
| 2016/0154892 A1 | 6/2016 | Carrier et al. | |
| 2016/0232155 A1* | 8/2016 | Allen | G06Q 10/06316 |
| 2016/0350486 A1 | 12/2016 | Plunkett et al. | |
| 2017/0012924 A1 | 1/2017 | Freeman et al. | |
| 2017/0039326 A1* | 2/2017 | Stankiewicz | G06F 16/93 |
| 2017/0039502 A1* | 2/2017 | Guman | G16H 10/60 |
| 2017/0091847 A1* | 3/2017 | Cama | G06Q 30/0629 |
| 2017/0220743 A1* | 8/2017 | Imler | G16H 40/20 |
| 2018/0046764 A1* | 2/2018 | Katwala | G06F 40/169 |
| 2018/0096105 A1* | 4/2018 | Bleicher | G16H 50/30 |
| 2018/0330730 A1* | 11/2018 | Garg | G10L 15/1815 |
| 2019/0140995 A1* | 5/2019 | Roller | G06F 40/295 |
| 2019/0180862 A1* | 6/2019 | Wisser | G16H 80/00 |

OTHER PUBLICATIONS

Office Action, dated Mar. 13, 2020, for U.S. Appl. No. 15/811,260, filed Nov. 13, 2017, invented by E. Erpenbach et al., Total 26 pages.
Office Action, dated Mar. 16, 2020, for U.S. Appl. No. 16/406,915, filed May 8, 2019, invented by E. Erpenbach et al., Total 23 pages.
H. Lee, "Paging Dr. Watson: IBM's Watson Supercomputer Now Being Used in Healthcare" (online) retrieved from the Internet on Oct. 8, 2017, at URL> http://library.ahima.org/doc?oid=300441#.WdrkTDBrxhE, Total 5 pages.
Wikipedia, "Named Entitiy-Recognition", (online), retrieved from the Internet on Oct. 10, 2017, at URL> https://en.wikipedia.org/wiki/Named-entity_recognitiondated . . . . Total 3 pages.
B. Kaur, "Review On Error Detection and Error Correction Techniques in NLP", dated Jun. 2014, International Journal of Advanced Research in Computer Science and Software Engineering, vol. 4, Issue 6, Total 3 pages.
U.S. Patent Application, dated Nov. 13, 2017, for U.S. Appl. No. 15/811,260, filed Nov. 13, 2017, invented by E. Erpenbach et al., Total 41 pages.
List of Patents or Patent Applications Treated as Related, dated Nov. 13, 2017, Total 2 pages.
U.S. Patent Application, dated May 8, 2019, for U.S. Appl. No. 16/406,885, filed May 8, 2019, invented by E. Erpenbach et al., Total 41 pages.
Peliminary Amendment, dated May 8, 2019, for U.S. Appl. No. 16/406,885, filed May 8, 2019, invented by E. Erpenbach et al., Total 8 pages.
Preliminary Amendment, dated Nov. 13, 2017, for U.S. Appl. No. 15/811,260, filed Nov. 13, 2017, invented by E. Erpenbach et al., Total 3 pages.
Preliminary Amendment, dated May 8, 2019, for U.S. Appl. No. 15/811,260, filed Nov. 13, 2017, invented by E. Erpenbach et al., Total 8 pages.
U.S. Patent Application, dated May 8, 2019, for U.S. Appl. No. 16/406,915, filed May 8, 2019, invented by E. Erpenbach et al., Total 41 pages.
Peliminary Amendment, dated May 8, 2019, for U.S. Appl. No. 16/406,915, filed May 8, 2019, invented by E. Erpenbach et al., Total 7 pages.
List of Patents or Application Treated as Related, dated May 8, 2019, Total 2 pages.
Office Action, dated Apr. 3, 2020, for U.S. Appl. No. 16/406,885, filed May 8, 2019, invented by E. Erpenbach et al., Total 31 pages.
Response to Office Action, dated Jun. 13, 2020, for U.S. Appl. No. 15/811,260, filed Nov. 13, 2017, invented by E. Erpenbach et al., Total 14 pages.
Final Office Actionl, dated Jun. 25, 2020, for U.S. Appl. No. 15/811,260, filed Nov. 13, 2017, invented by E. Erpenbach et al., Total 30 pages.
Response to Office Action, dated Jun. 13, 2020, for U.S. Appl. No. 16/406,915, filed May 8, 2019, invented by E. Erpenbach et al., Total 11 pages.
Final Office Actionl, dated Jun. 25, 2020, for U.S. Appl. No. 16/406,915, filed May 8, 2019, invented by E. Erpenbach et al., Total 29 pages.

(56) References Cited

OTHER PUBLICATIONS

Response to Office Action, dated Jul. 6, 2020, for U.S. Appl. No. 16/406,885, filed May 8, 2019, invented by E. Erpenbach et al., Total 13 pages.
Response to Final Office Action, dated Jun. 13, 2020, for U.S. Appl. No. 15/811,260, filed Nov. 13, 2017, invented by E. Erpenbach et al., Total 13 pages.
Response to Final Office Action, dated Jun. 13, 2020, for U.S. Appl. No. 16/406,915, filed May 8, 2019, invented by E. Erpenbach et al., Total 11 pages.
Final Office Action, dated Aug. 4, 2020, for U.S. Appl. No. 16/406,885, filed May 8, 2019, invented by E. Erpenbach et al., Total 33 pages.
Response to Final Office Action, filed Oct. 11, 2020, for U.S. Appl. No. 16/406,885, filed May 8, 2019, invented by E. Erpenbach et al., Total 15 pages.
Response to Final Office Action, dated Aug. 23, 2020, for U.S. Appl. No. 15/811,260, filed Nov. 13, 2017, invented by E. Erpenbach et al., Total 13 pages.
Response to Final Office Action, dated Aug. 23, 2020, for U.S. Appl. No. 16/406,915, filed May 8, 2019, invented by E. Erpenbach et al., Total 10 pages.
Office Action3, dated Nov. 30, 2020, for U.S. Appl. No. 16/406,885, filed May 8, 2019, invented by E. Erpenbach et al., Total 37 pages.
Response to Office Action, dated Mar. 1, 2021, for U.S. Appl. No. 16/406,885, filed May 8, 2019, invented by E. Erpenbach et al., Total 16 pages.
Office Actions, dated Nov. 30, 2020, for U.S. Appl. No. 15/811,260, filed Nov. 13, 2017, invented by E. Erpenbach et al., Total 32 pages.
Response to Office Action, dated Mar. 1, 2021, for U.S. Appl. No. 15/811,260, filed Nov. 13, 2017, invented by E. Erpenbach et al., Total 14 pages.
Office Actions, dated Dec. 3, 2020, for U.S. Appl. No. 16/406,915, filed May 8, 2019, invented by E. Erpenbach et al., Total 30 pages.
Response to Office Action, dated Mar. 1, 2021, for U.S. Appl. No. 16/406,915, filed May 8, 2019, invented by E. Erpenbach et al., Total 12 pages.
Interview Summary dated Oct. 9, 2020, for U.S. Appl. No. 16/406,885, filed May 8, 2019, invented by E. Erpenbach et al., Total 8 pages.
Interview Summary, dated Jul. 10, 2020, for U.S. Appl. No. 16/406,885, filed May 8, 2019, invented by E. Erpenbach et al., Total 8 pages.
Interview Summary dated Feb. 18, 2021, for U.S. Appl. No. 16/406,885, filed May 8, 2019, invented by E. Erpenbach et al., Total 6 pages.
Interview Summary, dated Jun. 15, 2020, for U.S. Appl. No. 15/811,260, filed Nov. 13, 2017, invented by E. Erpenbach et al., Total 4 pages.
Interview Summary, dated Aug. 19, 2020, for U.S. Appl. No. 15/811,260, filed Nov. 13, 2017, invented by E. Erpenbach et al., Total 4 pages.
Interview Summary, dated Feb. 18, 2021, for U.S. Appl. No. 15/811,260, filed Nov. 13, 2017, invented by E. Erpenbach et al., Total 2 pages.
Interview Summary, dated Aug. 19, 2020, for U.S. Appl. No. 16/406,915, filed May 8, 2019, invented by E. Erpenbach et al., Total 4 pages.
Interview Summary, dated Feb. 18, 2021, for U.S. Appl. No. 16/406,915, filed May 8, 2019, invented by E. Erpenbach et al., Total 2 pages.
Response to Final Office Action, dated Jun. 18, 2021, for U.S. Appl. No. 16/406,885, filed May 8, 2019, invented by E. Erpenbach et al., Total 12 pages.
Final Office Action, dated Apr. 5, 2021, for U.S. Appl. No. 16/406,885, filed May 8, 2019, invented by E. Erpenbach et al., Total 25 pages.
Notice of Allowance, dated May 18, 2021, for U.S. Appl. No. 15/811,260, filed Nov. 13, 2017, invented by E. Erpenbach et al., Total 29 pages.
Notice of Allowance, dated May 20, 2021, for U.S. Appl. No. 16/406,915, filed May 8, 2019, invented by E. Erpenbach et al., Total 27 pages.

\* cited by examiner

Interaction Information Package

User Interaction Information

NLP Item Priority Information

NLP Item Transmission

DETERMINING USER INTERACTIONS WITH NATURAL LANGUAGE PROCESSOR (NPL) ITEMS IN DOCUMENTS TO DETERMINE PRIORITIES TO PRESENT NPL ITEMS IN DOCUMENTS TO REVIEW

BACKGROUND OF THE INVENTION

1. Field of the Invention

The present invention relates to a computer program product, system, and method to determine priorities to present natural language processor (NLP) items items in documents to review.

2. Description of the Related Art

Natural language processing (NLP) of unstructured text documents allows a software system to extract concepts from the documents that can then be analyzed in order to present meaningful information to a user. For instance, medical documents (physician clinic notes, pathology reports, etc.) may be processed by the NLP system in order to extract a patient's diagnosis, past medical history, therapy history, and other data needed to evaluate a patient for the next steps in their treatment. With NLP processing, there may be errors in the processed data that may need to be corrected. Mistakes may be especially problematic if the errors are for mission critical information, like errors in medical information, such as patient medical conditions, diagnosis, current medication regimens, etc.

There is a need in the art to provide improved techniques for presenting users with NLP extracted information to review to optimize user interaction to review and correct errors in the NLP content.

SUMMARY

Provided are a computer program product, system, and method for determining user interactions with natural language processor (NLP) items in documents to determine priorities to present NLP items in documents to review. Information is received on user interactions with natural language processing (NLP) items in documents presented at least one computing device. Indication is made in a database of user interaction information on the user interactions with the NLP items indicated in the received transmitted information. The user interaction information in the database providing interaction information for NLP items in the selected document is used to determine an order of the NLP items in the selected document. Content of the NLP items in the selected document is transmitted to present to a reviewing user at a reviewing computing device in the determined order.

DETAILED DESCRIPTION

Figure 1:
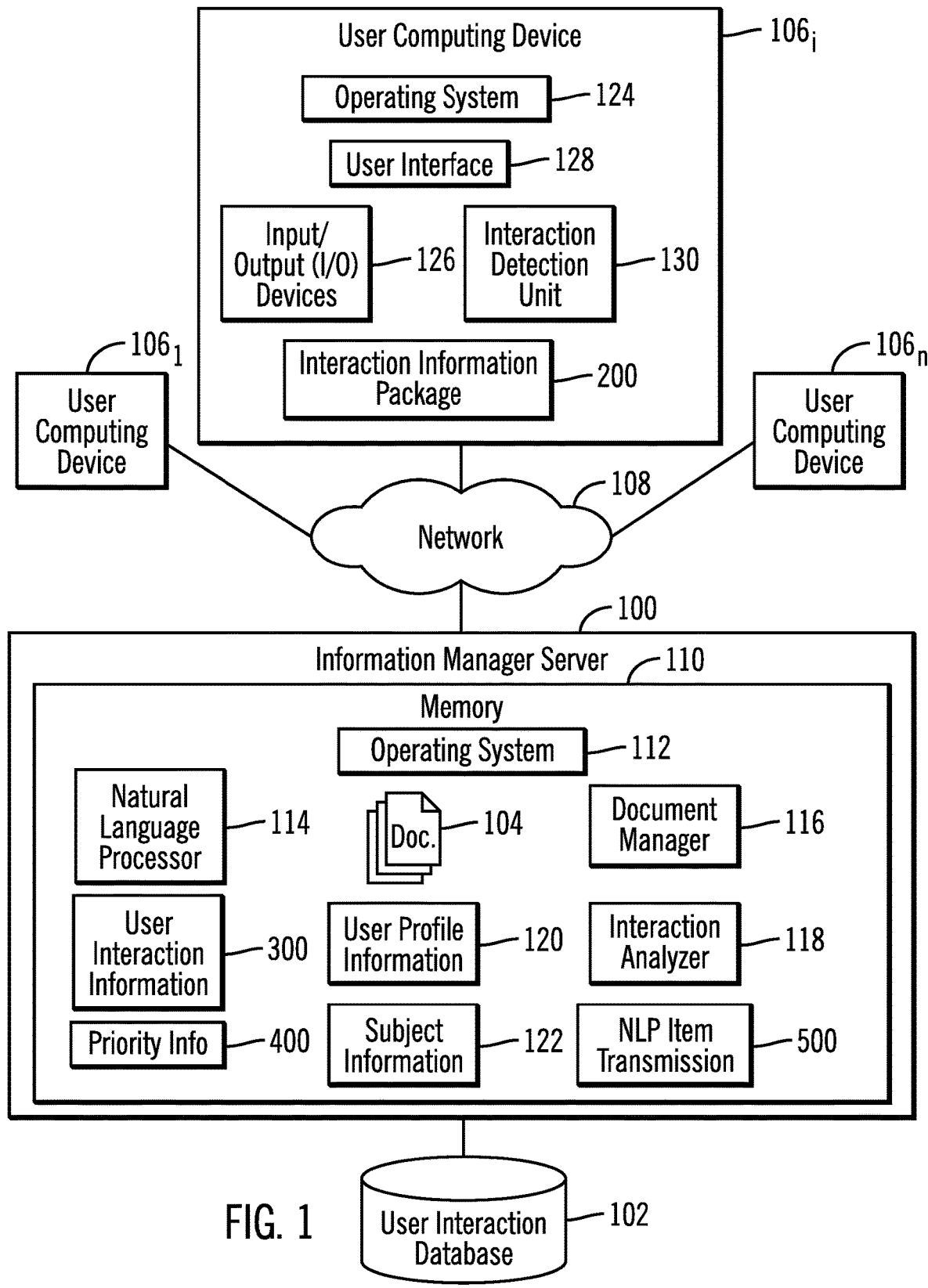
FIG. 1 illustrates an embodiment of a network information management environment.

NLP systems may need to present to user NLP items and content in a document to review or correct. However, users in a system may have limited time to review NLP items in a document to correct. In a medical record system, a doctor may be presented with a vast array of important NLP items in medical records to correct. This can consist of many screens of information, and it is often overwhelming to a user. In fact, a user may become so frustrated with having to correct so many NLP items, they may decide to avoid using the NLP correction and review system due to the time commitment.

Described embodiments provide techniques to observe user interaction with NLP items in a document to determine the interaction frequency with the NLP items and context attribute values related to interaction with the document. The gathered NLP item interaction information, along with context attribute values related to the context of the interaction, may be saved as user interaction in a computer database. When the NLP system is generating a document to present to a user, the NLP system may then consider interaction frequencies of NLP items in specific contexts, similar to the context with which the document will be reviewed, to determine a priority of NLP items based on their interaction frequency. This priority information may be used to determine an order in which the NLP items are presented to a user to review and correct, so that the user will focus on those NLP items collectively deemed by similar users in similar contexts in the system to be of high importance, as evidenced by their interaction frequency with the NLP items. The user may then focus on those NLP items they recognize as important and ignore or disregard the later presented NLP items having lower priority, as evidenced by a lower interaction frequency.

Described embodiments also provide improved techniques and data structures for gathering NLP item interaction information at the user computing devices to record the relevant information concerning the user interaction with the NLP items rendered in a computer user interface, including context attribute values related to the context of the interaction and the interaction frequency with the NLP items.

Described embodiments also provide improved computer database structures to improve the management of information on user interactions with NLP items and the context of that information to allow later database searching of the interaction information to generate priority values for the NLP items that are specific to the context attributes in which the interactions occurred. Examples of context attributes include user specific context, subject matter specific context of the NLP items, and NLP item specific attributes, such as interrogative sentences in which the NLP items were included. These improved database structures allow for focus on accessing NLP item information for specified context attribute values to use to determine a priority based on the interaction by users across documents in the network in similar context. The cumulative priority may then be used to determine an order in which NLP items should be presented to the user to review that reflects priority based on actual interaction by similarly situated users with the NLP items.

Described embodiments provide further improved computer technology to improve the way the user interface program of the user computer gathers user interactions with NLP items to provide to the server and to present NLP items to the user so as to optimize the user responses and corrections to NLP items in a document. With described embodiments, user computers detect interactions with natural language processing (NLP) items in documents and, for each interaction with an NLP item, each user computer sends interaction information to the server on the interaction including information on a context attribute value for a context attribute related to the interaction with the NLP item.

With described embodiments, multiple of the user computers gather their information on interactions with NLP items to send to the server to use to determine a priority value for the NLP items. When a user requests a document from the server, the server will provide an order for the NLP items in the requested document based on the NLP item interaction information from the plurality of computers. The user interface at the user computers then presents the NLP items in a requested document to the user in the order, determined according to the collective information on user interactions with the NLP items gathered by the user computers.

By presenting NLP items having errors to correct to a user in the user interface according to an order based on a priority determined by a frequency of access by similarly situated users to the NLP items priority of the NLP items, the system increases the likelihood the user responds to the highest priority NLP items to correct by first presenting those higher priority NLP items early in the ordering. In this way, the user is not overwhelmed by being presented with all the NLP items to correct, but is provided NLP items in an order determined by a frequency of access by similarly situated users to the NLP items. This presentation assists the user in focusing on first correcting those NLP items in the document having a highest priority, and when the user no longer has time or interest in correcting NLP items, those lower priority NLP items will be ignored, while the highest priority NLP items presented first for consideration to the user will likely have been corrected.

FIG. 1 illustrates an embodiment of an information retrieval environment having an information manager server 100 maintaining a user interaction database 102 having information on user interaction with documents 104 in the database 102. The information manager server 100 may communicate with a plurality of user computing devices $106_1$, $106_i$ ... $106_n$ over a network 108, where the users are recognized by the information manager server 100 to interact with the documents 104. The information manager server 100 includes a memory 110 including an operating system 112 to manage server 100 operations and interact with connected devices; a natural language processor 114, such as by way of example, the Watson™ Natural Language, to process the documents 104 to determine Natural Language Processor (NLP) items in the documents 104, which may comprise entities identified in the documents 104, such as classified named entities in the text classified into categories, such as names of persons, organizations, locations, expressions of times, terms and entities related to the subject matter of the documents 104, etc.; a document manager 116 to manage access to documents 104 in the user interaction database 102; and an interaction analyzer 118 to analyze and process user interaction information included in an interaction information package 200 transmitted from the user computing devices $106_1$, $106_i$ ... $106_n$.

The user interaction database 102 may include records and data structures, shown as maintained in the memory 110, including user profile information 120 having information on the users of the user computing devices $106_1$, $106_i$ ... $106_n$, including profiles related to positions or roles of the users in the environment in which the information manager server 100 is deployed; subject information 122 having information on subjects of the documents 104, i.e., to which the documents pertain 104, e.g., the subjects may comprise patients and the documents 104 may comprise patient medical records; user interaction information 300 generated by the interaction analyzer 118 to maintain information on user interaction with NLP items in documents 104; and NLP item priority information 400 having priority values for the NLP items calculated by the interaction analyzer 118 and used to determine an order in which the NLP items are presented to the users at the user computing devices $106_1$, $106_i$ ... $106_n$ to consider. The interaction analyzer 118 may generate an NLP item transmission 500 for a document providing an order with which to present the NLP items in the document for the user to review.

The user interaction database 102 may comprise a relational or object oriented database, or other suitable database types.

In one embodiment, the documents 104 may comprise medical records and the subjects may comprise patients for which the medical records 106 are maintained. A medical record 106 may include numerous interrogatory sentences asking questions about the subject/patient's medical history, personal history, current diagnosis, current medication, etc., comprising the NLP items. Thus the NLP items may comprise objects of the interrogatory sentences or other patient and medical information the users enter into the medical records. The users may comprise doctors, nurses, and other medical professionals that may add information to the medical records. The documents 104 may comprise a structured or unstructured document, and be in a format such as Extended Markup Language (XML), Hypertext Markup Language (HTML), a text format, word processor format, etc.

The user computing devices $106_1$, $106_i$ ... $106_n$, may include, as shown with user computing device $106_i$, an operating system 124 to manage and interact with (Input/Output I/O) devices 126, a user interface 128 in which to render documents 104 from the information manager server 100 and allow the user to interact with the documents 104 with the I/O devices 126; and interaction detection unit 130 to detect user interactions with the NLP items in the document 104 rendered in the user interface 128 with the I/O devices 132; and interaction information package 200 generated by the interaction detection unit 130, including information on user interaction with NLP items in a document 104 rendered in the user interface 128.

In one embodiment the I/O devices 126 may comprise a mouse, keyboard, etc., and the interactions may comprise the user selecting or entering content for the NLP items in the document 104 rendered in the user interface 128. The I/O device 126 may further comprise a gaze tracking device to determine an NLP item in the document or interrogative sentence including the NLP item at which the user is gazing. A gaze tracking device is typically worn as glasses and includes cameras on the glasses to acquire gazed text or images being gazed by the eyes of the user. The gaze tracking device includes a camera to capture and analyze an eye image to determine the pupil location to acquire the gazed image or text the user eyes are staring at or tracking, i.e., gazing at directly. The interaction detecting unit 130 may determine the NLP item or interrogative sentence including the NLP item with which the user is interacting, such as selecting with a mouse pointer, entering text for with a keyboard, or gazing at with a gaze tracking glasses.

The user computing devices $106_1$, $106_i$ ... $106_n$, may comprise a smart phone, tablet, personal digital assistance (PDA), laptop, or stationary computing device, e.g., desktop computer, server. The memory 110 may comprise non-volatile and/or volatile memory types, such as a Flash Memory (NAND dies of flash memory cells), a non-volatile dual in-line memory module (NVDIMM), DIMM, Static Random Access Memory (SRAM), ferroelectric random-access memory (FeTRAM), Random Access Memory (RAM) drive, Dynamic RAM (DRAM), storage-class memory (SCM), Phase Change Memory (PCM), resistive random access memory (RRAM), spin transfer torque memory (STM-RAM), conductive bridging RAM (CBRAM), nanowire-based non-volatile memory, magnetoresistive random-access memory (MRAM), and other electrically erasable programmable read only memory (EEPROM) type devices, hard disk drives, removable memory/storage devices, etc.

The user interactive database 102 may be implemented in one or more storage devices, such as magnetic hard disk drives, solid state storage device (SSD) comprised of solid state electronics, EEPROM (Electrically Erasable Programmable Read-Only Memory), flash memory, flash disk, Random Access Memory (RAM) drive, storage-class memory (SCM), etc., Phase Change Memory (PCM), resistive random access memory (RRAM), spin transfer torque memory (STT-RAM), conductive bridging RAM (CBRAM), magnetic hard disk drive, optical disk, tape, etc. Data in the storages $102_1$, $102_2$ ... $102_n$, 4 may further be configured from an array of devices, such as Just a Bunch of Disks (JBOD), Direct Access Storage Device (DASD), Redundant Array of Independent Disks (RAID) array, virtualization device, etc.

The network 108 may comprise one or more networks including Local Area Networks (LAN), Storage Area Networks (SAN), Wide Area Network (WAN), peer-to-peer network, wireless network, the Internet, etc.

Generally, program modules, such as the program components 112, 114, 116, 118, 124, 128, 130, and any others described herein, may comprise routines, programs, objects, components, logic, data structures, and so on that perform particular tasks or implement particular abstract data types. The program modules may be practiced in distributed cloud computing environments where tasks are performed by remote processing devices that are linked through a communications network. In a distributed cloud computing environment, program modules may be located in both local and remote computer system storage media including memory storage devices.

The program components and hardware devices of the user computing devices $106_1$, $106_i$ ... $106_n$ and information management server 100 of FIG. 1 may be implemented in one or more computer systems, where if they are implemented in multiple computer systems, then the computer systems may communicate over a network.

The program components 112, 114, 116, 118, 124, 128, 130, and any others described herein, may be accessed by a processor from memory to execute. Alternatively, some or all of the program components 112, 114, 116, 118, 124, 128, 130, and any others described herein, may be implemented in separate hardware devices, such as Application Specific Integrated Circuit (ASIC) hardware devices.

The functions described as performed by the program components 112, 114, 116, 118, 124, 128, 130, and any others described herein, may be implemented as program code in fewer program modules than shown or implemented as program code throughout a greater number of program modules than shown.

Figure 2:
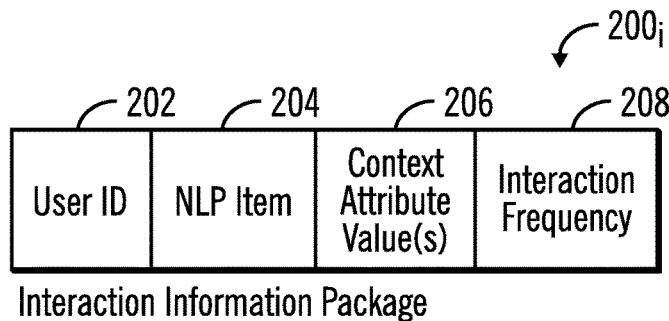
FIG. 2 illustrates an embodiment of an interaction information package sent form a user computing device on interactions with Natural Language Processor (NLP) items.

FIG. 2 illustrates an embodiment of an interaction information package $200_i$ generated by the interaction detection unit 130 in a user computing device $106_i$ and includes a user identifier 202 of the user interacting with the user interface 128 when the interaction information package $200_i$ was generated; an NLP item 204 for which the interaction was detected; one or more context attribute values 206 for context attributes related to the user interaction with the NLP item 204 and an interaction frequency 208 indicating one or more distinct interactions with the NLP item 204.

Figure 3:
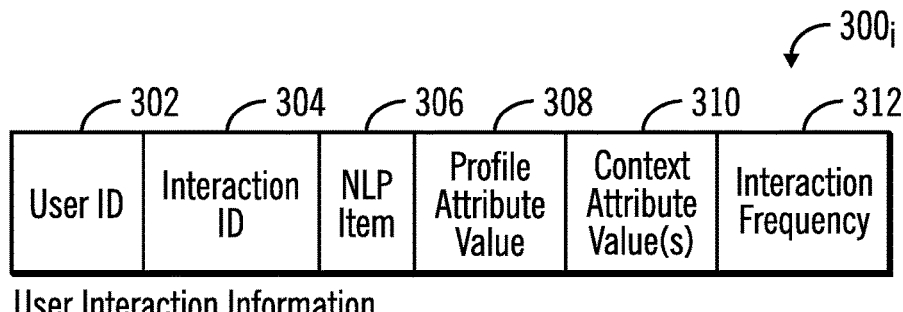
FIG. 3 illustrates an embodiment of user interaction information on interaction with NLP items.

FIG. 3 illustrates an embodiment of user interaction information $300_i$ generated by the interaction analyzer 118 from a received interaction information package $200_i$, and includes a user identifier 302 of the user interacting with the NLP item 306, which may be optional; and interaction ID 304 uniquely identifying the user interaction information $300_i$; the NLP item 306 subject to the interaction; one or more profile attribute values 308 of profiles of the user 302, such as role in an organization, position, personal identification information, etc.; one or more context attribute values 310 from those 206 included in the interaction information package 200; and an interaction frequency 312 also from the corresponding field 208 in the interaction information package $200_i$.

Figure 4:
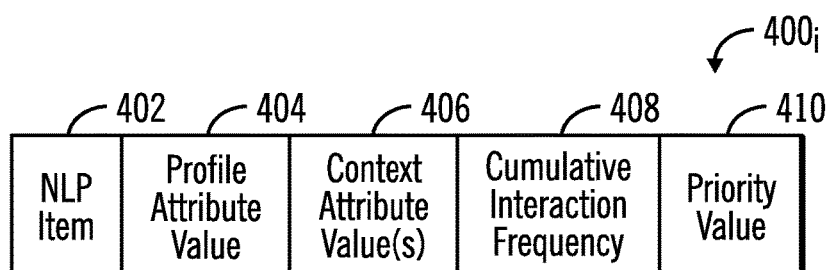
FIG. 4 illustrates an embodiment of NLP item priority information.

FIG. 4 illustrates an embodiment of an instance of NLP item priority information $400_i$, which may be generated at the time a document 104 is selected to provide to a user to review or may be generated in advance to be available when a document is selected, and periodically updated. The NLP item priority information $400_i$ includes the NLP item 402 for which the value is generated; a profile attribute value 404 of the users whose interactions were considered to calculate the priority value; one or more context attribute values 406 related to the context in which users whose interactions were considered to calculate the priority value interacted with the NLP item 402; a cumulative interaction frequency 408 comprising the total or combination of the interaction frequencies 312 from all interaction information instances $300_i$ having NLP item 306, profile attribute value 308, and context attribute values 310 matching those 402, 404, and 406 of the priority value 410 being calculated; and a priority value 410 derived from the cumulative interaction frequency 408. The priority value 410 may be determined based on a priority range the number of interactions 408 falls within, high, medium, low, etc., or may be calculated as a percentage of the interactions for an NLP item 402 across context attributes and profiles, or within context attributes and profiles.

Figure 5:
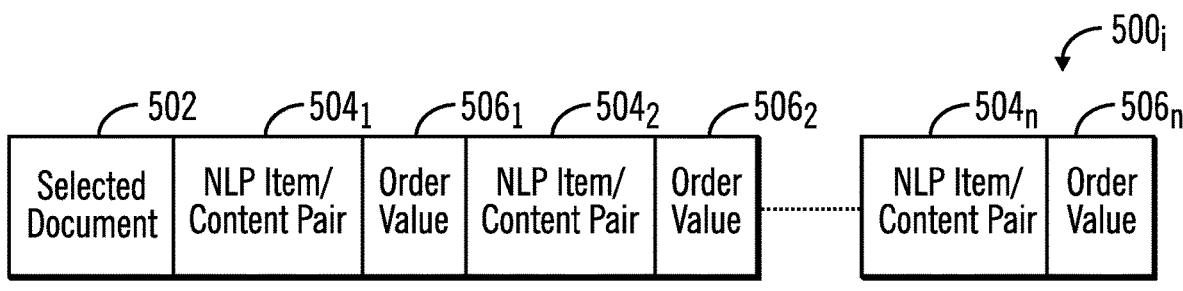
FIG. 5 illustrates an embodiment of an NLP item transmission.

FIG. 5 illustrates an embodiment of an instance of an NLP item transmission $500_i$ sent to a user computing device $106_1$, $106_i$ . . . $106_n$, including indication or a copy of a selected document 502 for which the transmission applies and for each of the NLP items within the selected document 502, a NLP item/content pair $504_1$, $504_2$ . . . $504_n$ and an order value $506_1$, $506_2$ . . . $506_n$ indicating an order in which the NLP item will be presented to the user in the user interface 128. The NLP item $504_i$ information may further indicate a location in the selected document 502 of the NLP item $504_1$.

Figure 6:
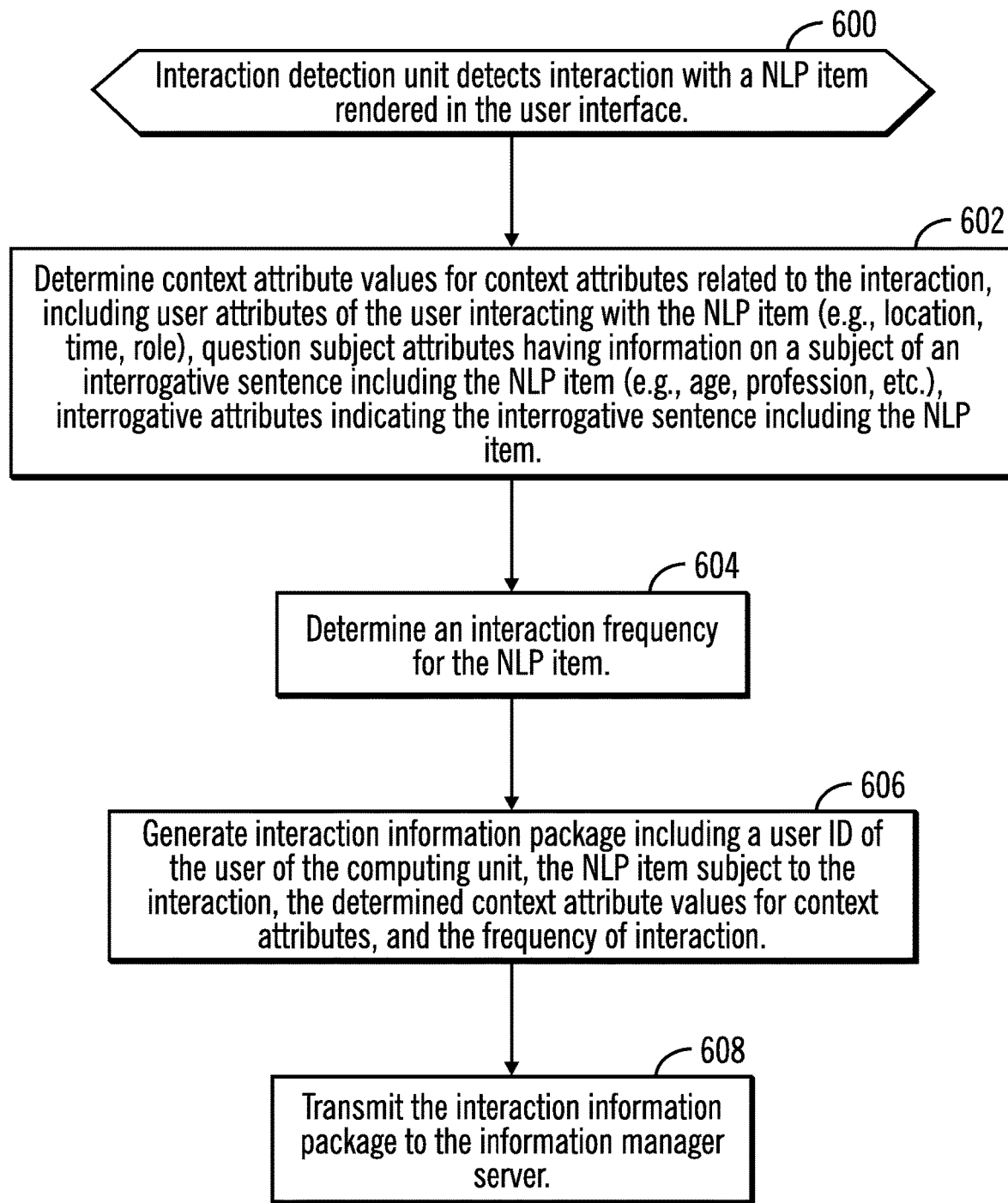
FIG. 6 illustrates an embodiment of operations at an interacting user computing device to detect interactions with NLP items and generate the interaction information package.

FIG. 6 illustrates an embodiment of operations performed by the interaction detection unit 130 in a user computing device $106_i$ to provide the information management server 100 with information on a user interaction at the user computing device $106_i$ with an NLP element in a document 104 rendered in the user interface 128. Upon the interaction detection unit 130 detecting (at block 600) an interaction with an NLP item rendered in the user interface 128 through an I/O device 126, the interaction detection unit 130 determines (at block 602) context attribute values for context attributes related to the interaction, including user attributes of the user interacting with the NLP item (e.g., location, time, cohorts or groups in which the user is included), a question subject attributes having information on a subject of an interrogative sentence including the NLP item (e.g., age, profession, etc.), and NLP specific attribute values, such as an interrogative sentence including the NLP item. For instance, the location may be determined from a location indicated in the user computing device $106_i$, such as from stored information or information from a Global Positioning System (GPS) device, and the time may be determined from the system time at the device $106_i$. Context attribute values based on the content of the document 104 being rendered, such as an interrogative sentence, may be determined by using NLP algorithms to analyze the sentence structure including the NLP item subject to the interaction. The interaction frequency with the NLP item is determined (at block 604), which may be one or more times if there are multiple distinct interactions as determined by the interaction detection unit 130.

A user interaction may comprise the user entering information for an NLP item, such as an answer to an interrogative question, considering the NLP item, as evidenced by detection of mouse/keyboard interaction or gazing at a sentence including the NLP item.

The interaction detection unit 130 generates (at block 606) an interaction information package $200_i$ including a user ID 202 of the user of the user computing device $106_i$ computing unit, the NLP item 204 subject to the interaction and the determined context attribute values 206 and interaction frequency 208. The interaction information package $200_i$ is then transmitted (at block 608) to the information manager server 100. An interaction information package $200_i$ may include information for just interaction with one or multiple NLP items in the document 104.

With the embodiment of FIG. 6, the user computing device $106_i$ gathers directly information on how the user interacts with the NLP items, which may comprise answers to an interrogative sentence. This information may then be combined with such interaction information from multiple users to determine an importance of an NLP item as evidenced by cumulative user interaction with that item. The information manager server 100 may then use this interaction information to determine priorities for NLP items to determine an order in which to present NLP items to the users to review at a later time, so that users are provided first NLP items having a highest interaction rate or considered most by users to optimize the user response rate to review NLP items. This provides users with NLP items to review based on their own previous selection of NLP items they prioritized when they were reviewing other documents. Presenting to a user NLP items to consider in an order based on the rate of interaction with NLP items by the user and their cohorts increases the likelihood that the user will review the presented NLP items, because they are presented in an order of importance determined by their own previous considerations and interactions.

Figure 7:
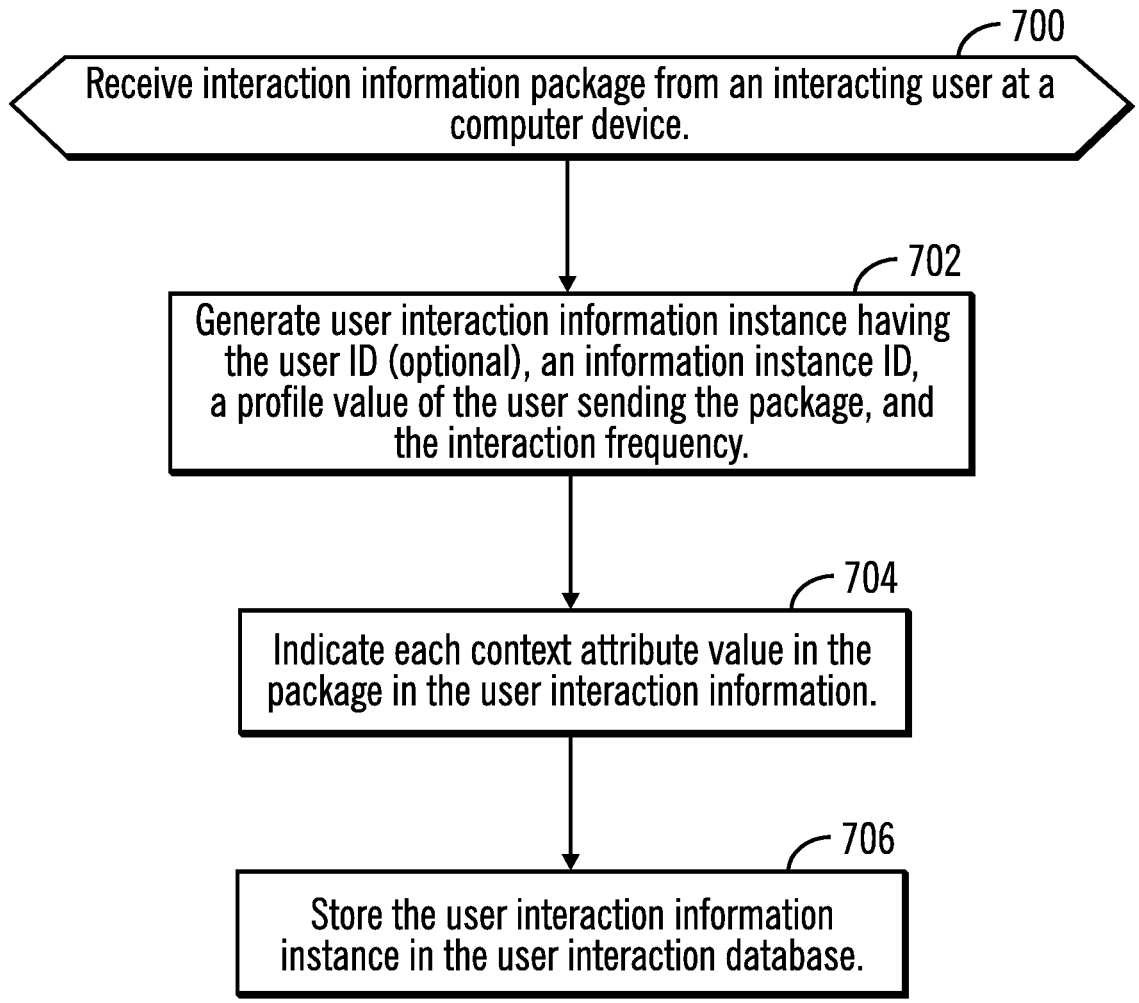
FIG. 7 illustrates an embodiment of operations to process an interaction information package to generate user interaction information.

FIG. 7 illustrates an embodiment of operations performed by the interaction analyzer 118 to process a received interaction information package $200_i$. Upon receiving (at block 700) an interaction information package $200_i$ from an interacting user at a computing device $106_1$, the interaction analyzer 118 generates (at block 702) a user interaction information $300_i$ instance having the user ID 302 (optional) of the interacting user at the user computing device $106_i$ that sent the package $200_i$, an information instance ID 304, a profile attribute value of the user sending the package $200_i$, which may be determined from the user profile information 120 or sent in the package $200_i$, and the interaction frequency 312 as indicated in field 208 of the package $200_i$. Each context attribute value 206 in the interaction information package $200_i$ is indicated (at block 704) in a context attribute value 310 filed in the user interaction information instance $300_i$. The generated user interaction information $300_i$ may then be stored (at block 706) in the user interaction database 102, such as a database record or object.

With the embodiment of FIG. 7, the information manager server 100 maintains information on interactions with each NLP item in different database records across all users in the system to allow for database operations to search and combine information based on NLP items, user profiles, and context attribute values.

Figure 8:
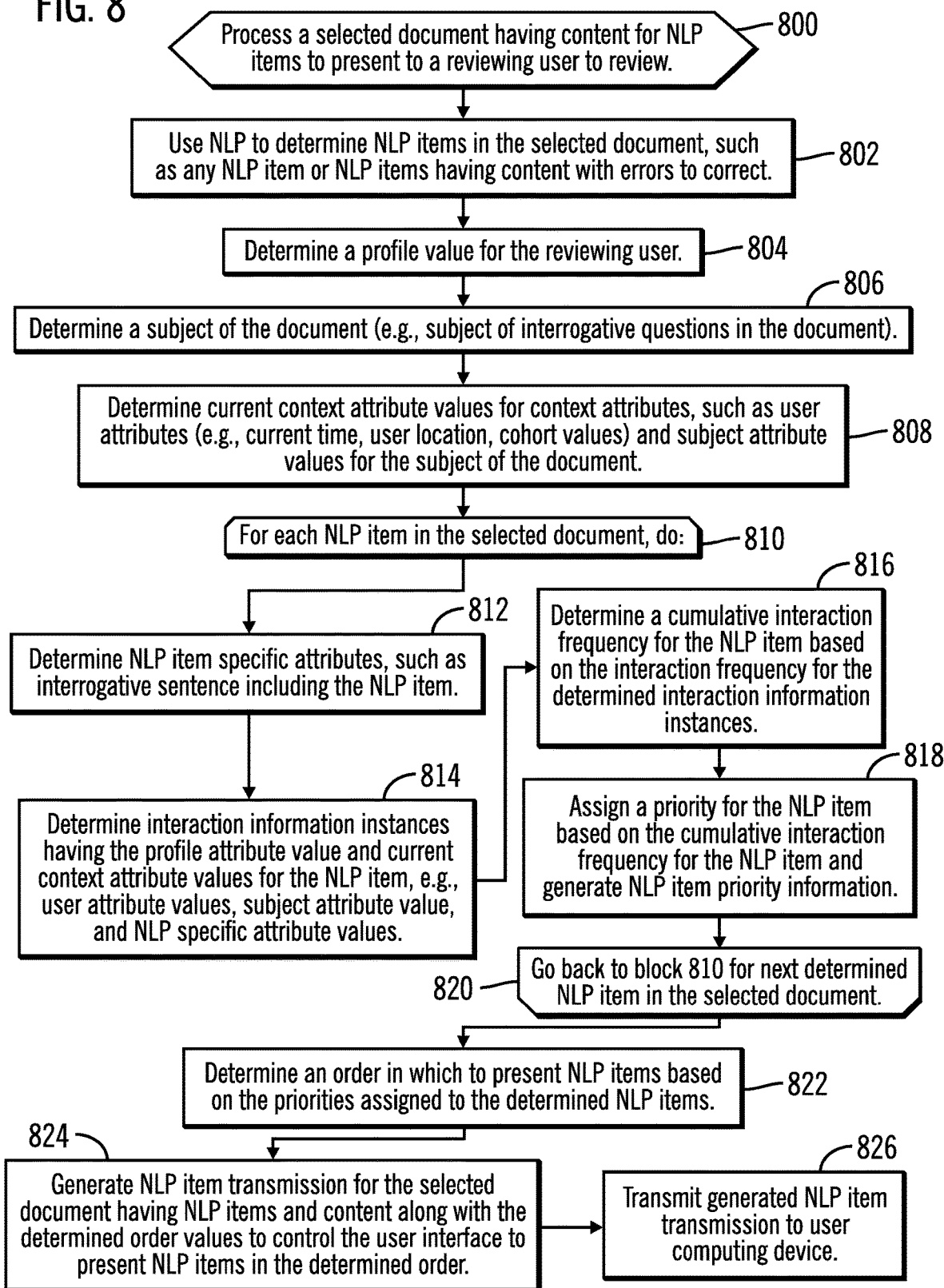
FIG. 8 illustrates an embodiment of operations to process user interaction information in a user interaction database to generate priorities for NLP items used to determine an order for presenting NLP items to a reviewing user.

FIG. 8 illustrates an embodiment of operations performed by the interaction analyzer 118 to determine an order in which to present NLP items in a selected document 104 to be viewed in the user interface 128 of a user computing device $106_1$ of a reviewing user. This operation may be initiated when a reviewing user selects a document 104 to review. Upon processing (at block 800) a selected document having NLP items, the interaction analyzer 118 calls (at block 802) the NLP 114 to determine NLP items in the selected document 104, such as any NLP item or NLP items having content to review or with errors to correct. A profile value of the reviewing user to which the document 104 will be sent is determined (at block 804), which may be determined from the user profile information 120, such as a role of the reviewing user in the organization. A subject of the selected document 104 is determined (at block 806), this may be a person or entity associated with the document 104, such as a patient associated with a medical record of their medical information. The subject may also be determined by processing the document to determine if a person is identified as the subject of the document, such as the subject of an interrogative question requesting the identity of the person for which the document 104 is provided.

The interaction analyzer 118 determines (at block 808) current context attribute values for context attributes, including user context attributes, such as a current time, the current location of the user computing device $106_i$, cohort values of groups of users in which the user is included, such as an experience level, specific job title, etc., and subject attribute values for the subject of the document, such as personal information on the person that is the subject matter of the document 104, e.g., age, personal or sensitive information of relevance, etc.

The interaction analyzer 118 then performs a loop of operations at block 810 through 820 for each NLP item in the selected document 104. At block 812, the interaction analyzer 118 determines NLP item specific attributes in the selected document 104, such as an interrogative sentence or other information specific to the NLP item being considered. The interaction analyzer 118 may then initiate a query of the user interaction database 102 to determine (at block 814) user interaction information instances $300_i$ having the profile attribute value 308 and current context attribute values 310 for the NLP item 306 being considered, e.g., user attribute values, subject attribute value, and NLP specific attribute values, etc., to access the user interaction information instances $300_i$ relevant to the current user access of the document 104. The interaction analyzer 118 determines (at block 816) a cumulative interaction frequency 408 for the NLP item based on the interaction frequency 312 for each of the determined relevant interaction information instances $300_i$. The cumulative interaction frequency 408 may comprise the sum of interaction frequencies 312 for all the determined interaction information instances, or comprise some derived value, such as the some of the interaction frequencies 312 weighted or as a percentage of interactive frequencies across profile or context attributes for the NLP item.

The interaction analyzer 118 may then assign (at block 818) a priority value 410 for the NLP item based on the cumulative interaction frequency 408, and generate NLP item priority information $400_i$, having the NLP item 402 and fields/parameters used to search, including profile attribute value 404 and context attribute values 406, the determined cumulative interaction frequency 408 and priority value 410. This NLP item priority information $400_i$ may be stored in the user interaction database 102 or maintained temporarily and continually recalculated when needed for a document 104 to provide to a reviewing user.

After determining the priority values 410 for all the NLP items in the document 104, the interaction analyzer 118 determines (at block 822) an order in which to present NLP items based on the priority values 410 assigned to the determined NLP items. For instance, NLP items with higher priorities would be presented to the reviewing user before NLP items with a lower priority or lower level of interaction. An NLP item transmission $500_i$ is generated (at block 824) for the selected document 502 having NLP items and content $504_1, 504_2 \ldots 504_n$, along with the determined order values $506_1, 506_2 \ldots 506_n$, to control the user interface 128 to present NLP items in the determined order. The generated NLP item transmission $500_i$ is then transmitted (at block 826) to the user computing device $106_1$. The user interface 128 would use the order values $506_1, 506_2 \ldots 506_n$, to determine the order in which to present the NLP items and content $504_1, 504_2 \ldots 504_n$, in the selected document 502 to the user to review. In one embodiment, the NLP item transmission $500_i$ may not include NLP items of lower priority so as not to burden the reviewing user with too many items to consider. In this way, the NLP item transmission $500_i$ may only include a subset of the NLP items in the document 502 having a high priority value 410. Alternatively, the user may be presented with the lower priority NLP items later at a time they are less likely to continue with their review.

The described embodiments of FIG. 8 provide a database driven computer solution to maintaining information on user interaction with NLP items in documents to use to determine an order in which to present to the NLP items in a selected document to review. Described embodiments determine priorities of NLP items based on interactions with those same NLP items across users. Described embodiments may further only consider those interactions having context attributes that are relevant to the current context attributes for the presentation of the document. In this way, interaction frequency of NLP items being considered to determine the NLP item priority is specific to the current attributes that are present during the current document viewing, such as user specific context attributes, location, time, cohorts, and attributes specific to the subject of the document 104, such as patient or person to which the document pertains, as well as NLP specific items, such as an interrogative sentence in which the NLP item is considered. In this way the current calculated priority for the NLP items are specific to the use in which the document will be presented and will accurately reflect the priority that the user will expect.

Figure 9:
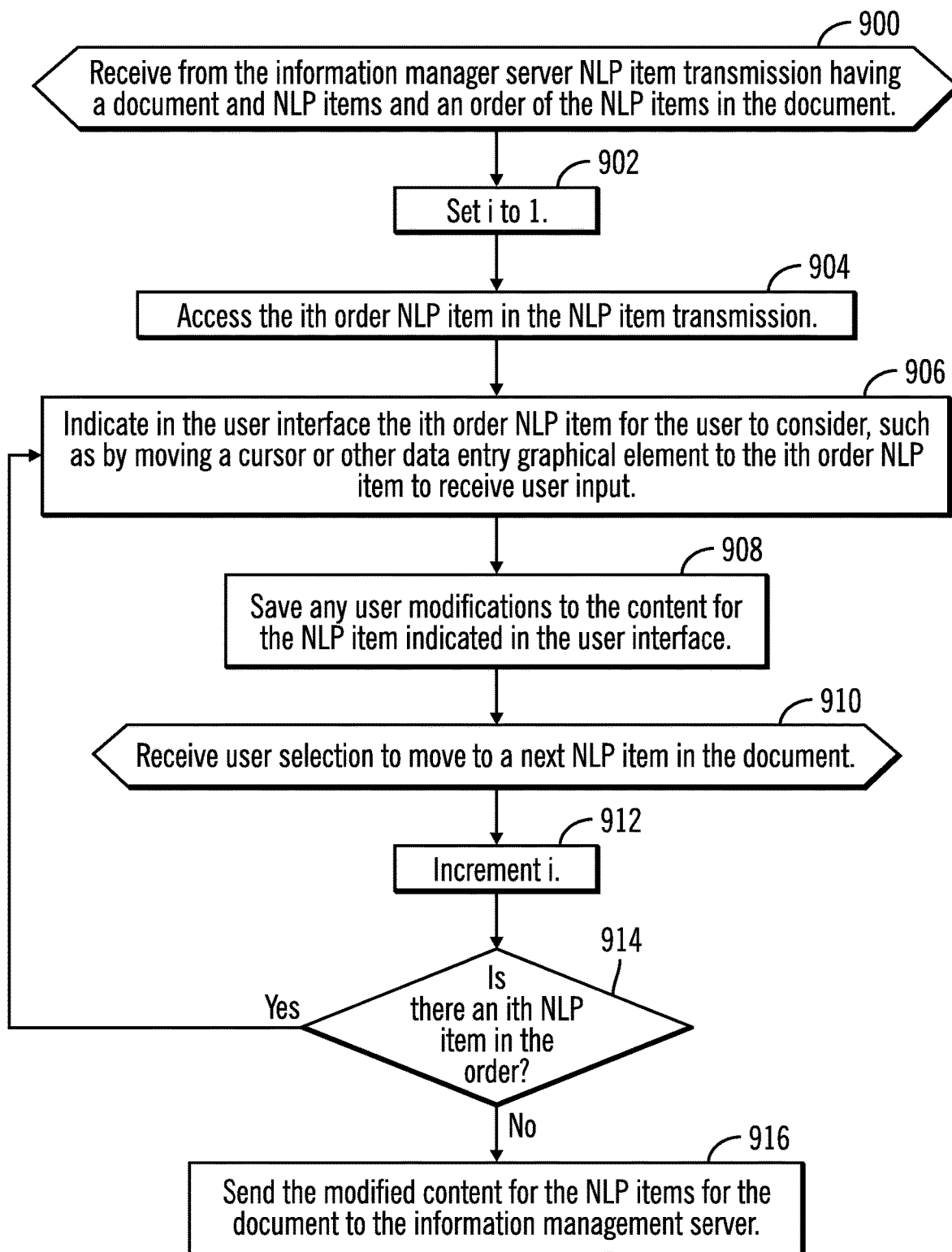
FIG. 9 illustrates an embodiment of operations to detect and send information on user interaction with NLP items and to render NLP items in a document in a user interface according to an ordering based on the user interactions.

FIG. 9 illustrates an embodiment of operations performed by the user interface 128 of the user computing device $106_i$ to render NLP items in a document 502 provided with the NLP item transmission $500_i$. Upon receiving (at block 900) from the information manager server 100 an NLP item transmission $500_i$ having a document 502 and NLP items $504_1 \ldots 504_n$ and an order $506_i \ldots 506_n$ of the NLP items in the document 502, the user interface 128 sets (at block 902) a variable i to one. The ith ordered NLP item $504_i$ having the order $506_1$ is accessed in the NLP transmission $500_i$. Indication is made (at block 906) in the user interface 128 of the ith ordered NLP item for the user to consider, such as by moving a cursor or other data entry graphical element to the ith order NLP item $504_1$ in the user interface 128 to enable the user to enter content for the NLP item $504_1$. Any user modification to the content for the NLP item $504_1$ indicated in the user interface 128 is saved (at block 908).

Upon receiving (at block 910) user selection to move to a next NLP item in the document 502, the variable i is incremented (at block 912) and if (at block 914) there is a next (i+1)th NLP item $504_{i+1}$ in the order $506_{i+1}$, then control proceeds to block 906 to indicate that next NLP item. If all NLP items in the order of the NLP transmission $500_i$ have been considered, which may comprise just a subset of the NLP items in the document 502, then the user computing device $106_1$ may send (at block 916) the modified content for the NLP items for the document 502 to the information management server 100 to store for the document 502/104.

With the embodiment of operations for FIG. 9, the user interface 128 may guide the user to the NLP items in the document according to the order based on a priority assigned to the NLP items, which is calculated based on the frequency of access of the NLP items by users in a context and having similar roles to the context/user role at the user computing device $100_i$. In this way, the user interface 128 is able to direct the user to those NLP items to correct having most priority or relevance to similarly situated users in the system to optimize the user response to correcting the NLP items.

Figure 10:
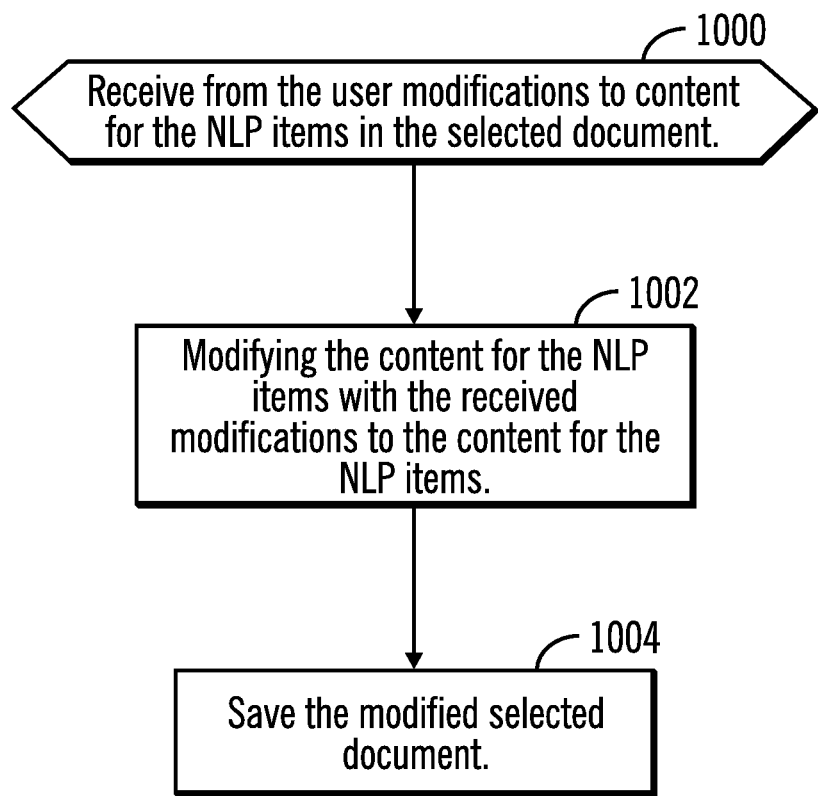
FIG. 10 illustrates an embodiment of operations to process modifications to NLP items from the reviewing user.

FIG. 10 illustrates an embodiment of operations performed by the document manager 116 to process changes to content for NLP items received from a user computing device $106_i$ in response to the user reviewing NLP items presented in an order according to the interaction priority. Upon receiving (at block 1000) the user modifications to content for NLP items in the selected document 104 presented to the user, the document manager 116 modifies (at block 1002) the content for the NLP items in the document 104 with the received modifications to the content for the NLP items. The modified document 104 is then saved (at block 1004), such as in the user interaction database 102.

With the described embodiments, NLP items with a lower priority may not be presented to the reviewing user to review. However, the user may also be able to access the full set of NLP items that are not prioritized as high. The observation and tracking of NLP item interaction can be performed at various user levels. At a single user level, the interactions of a single user may be observed. For instance, a doctor may frequently check and correct an NLP item with a certain attribute, but also have to access additional NLP items at the same time. All these interactions would be recorded. Further, interactions with NLP items may be considered at a group level, such interactions of a group of users sharing a group profile attribute. For instance, in a medical environment, the pulmonologists may focus on interacting with respiratory related medical information, whereas an oncologist may focus on cancer related NLP items. Other examples of groupings of users could be pathologists that verify and correct certain pathology items, and surgeons that verify and correct other surgery-related items. User roles can be determined using a staff directory such as in the user profile information 120.

NLP items can also be considered that have certain additional attribute contexts, such that NLP items may only be considered that have a location attribute of the location of the reviewing user may be considered. For instance, when a doctor is in a clinical workroom meeting with patients, the doctor may only interact with a few NLP items in the patient record. However, the doctor in their office or at home may interact with NLP items in greater detail because in such settings they have more time to carefully consider patient information. Furthermore, the doctor may work at multiple clinic locations, one of which is the primary hospital treating patients with critical needs, and an alternate regional location that is used for regular follow-up with patients that are not in an urgent care situation, and the doctors consistent differences in interactions with NLP items at the different locations would be observed and recorded in user interaction information instances. This allows customization of the priority of NLP items based on their location.

NLP item interaction frequency may also be distinguished based on the time of day at which the user is interacting with the system. For a doctor, the beginning of the day at the clinic, such as cancer center, can be hectic, and the doctor may have very limited time to review NLP items in the medical report as they have to meet with many patients. At other times of the day, such as in the afternoon, the doctors may have more time to work with a single patient, and may review more details and NLP items in the medical record. The described embodiments record the patterns of what attributes affect the interaction frequency of different NLP items for different times of a day.

An age of patient context attribute could be considered when determining what NLP data is reviewed and corrected by the doctor. The system may record that when pediatric patients are involved, the doctor prefers to review and correct certain NLP items, versus for elderly patients. Described embodiments can observe the interactions and classify NLP item review and corrections needs based on observing what the doctor reviews and corrects for different ages of patients.

A cohort of user attributes may provide a more fined grained categorization of a group in which the reviewing user is considered. For instance, in addition to recognizing that a doctor is a Leukemia doctor, there are more fine grained categorizations of cohorts of users, such as "leukemia doctors with 10 or more years of experience", "leukemia doctors who specialize in Acute Myeloid Leukemia (AML) leukemia patients", "general oncologist who sees leukemia, lung, melanoma, and many other cancer types", other classifications of users may also be provided that are observed to have a correlation with interactions with NLP items. The system could observe the NLP corrections for each user, and over time may be able to see patterns that for a certain cohort of users (e.g. AML leukemia specialists), certain NLP correction and review is common.

Upon making these observations over time, the NLP items that are frequently corrected by a user, or by a particular user-role (such as Leukemia doctors), can be prioritized higher as items that should be presented to the user in that cohort of users. Likewise, items that are infrequently reviewed or corrected may be prioritized lower over time because they are generally considered less by this user or user-role. The user interface 128 can monitor which NLP items are modified and based on the frequency count, can see which types of data are updated. The high priority NLP derived attributes can be presented to the user as the items that need immediate review. The user could also be given an option to see additional NLP derived attributes, but the user could focus on those high priority items if they have limited time. If the system has no high priority NLP derived attributes that need correction (that is, it has confidence that it already has the data it needs), then the user would not be prompted for any NLP corrections.

The reference characters used herein, such as i and n are used to denote a variable number of instances of an element, which may represent the same or different values, and may represent the same or different value when used with different or the same elements in different described instances.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The computational components of FIG. 1, including the user computing devices 106$_1$, 106$_i$ . . . 106$_n$ and information manager server 100, may be implemented in one or more computer systems, such as the computer system 1002 shown in FIG. 10. Computer system/server 1002 may be described in the general context of computer system executable instructions, such as program modules, being executed by a computer system. Generally, program modules may include routines, programs, objects, components, logic, data structures, and so on that perform particular tasks or implement particular abstract data types. Computer system/server 1002 may be practiced in distributed cloud computing environments where tasks are performed by remote processing devices that are linked through a communications network. In a distributed cloud computing environment, program modules may be located in both local and remote computer system storage media including memory storage devices.

Figure 11:
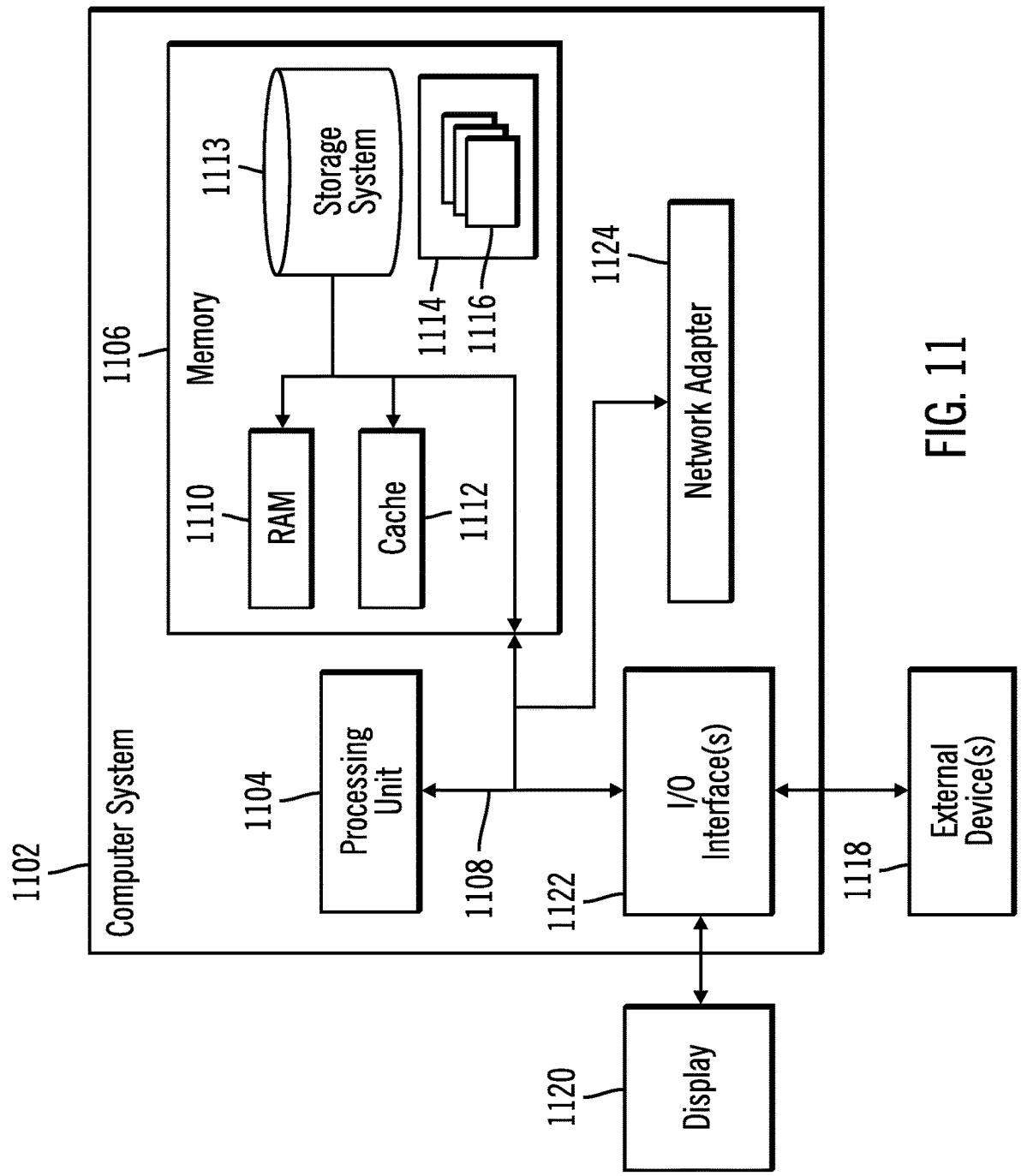
FIG. 11 illustrates a computing environment in which the components of FIG. 1 may be implemented.

As shown in FIG. 11, the computer system/server 1102 is shown in the form of a general-purpose computing device. The components of computer system/server 1102 may include, but are not limited to, one or more processors or processing units 1104, a system memory 1106, and a bus 1108 that couples various system components including system memory 1106 to processor 1104. Bus 1108 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 1102 typically includes a variety of computer system readable media. Such media may be any available media that is accessible by computer system/server 1102, and it includes both volatile and non-volatile media, removable and non-removable media.

System memory 1106 can include computer system readable media in the form of volatile memory, such as random access memory (RAM) 1110 and/or cache memory 1112.

Computer system/server 1102 may further include other removable/non-removable, volatile/non-volatile computer system storage media. By way of example only, storage system 1113 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 1108 by one or more data media interfaces. As will be further depicted and described below, memory 1106 may include at least one program product having a set (e.g., at least one) of program modules that are configured to carry out the functions of embodiments of the invention.

Program/utility 1114, having a set (at least one) of program modules 1116, may be stored in memory 1106 by way of example, and not limitation, as well as an operating system, one or more application programs, other program modules, and program data. Each of the operating system, one or more application programs, other program modules, and program data or some combination thereof, may include an implementation of a networking environment. The components of the computer 1102 may be implemented as program modules 1116 which generally carry out the functions and/or methodologies of embodiments of the invention as described herein. The systems of FIG. 1 may be implemented in one or more computer systems 1102, where if they are implemented in multiple computer systems 1102, then the computer systems may communicate over a network.

Computer system/server 1102 may also communicate with one or more external devices 1118 such as a keyboard, a pointing device, a display 1120, etc.; one or more devices that enable a user to interact with computer system/server 1102; and/or any devices (e.g., network card, modem, etc.) that enable computer system/server 1102 to communicate with one or more other computing devices. Such communication can occur via Input/Output (I/O) interfaces 1122. Still yet, computer system/server 1102 can communicate with one or more networks such as a local area network (LAN), a general wide area network (WAN), and/or a public network (e.g., the Internet) via network adapter 1124. As depicted, network adapter 1124 communicates with the other components of computer system/server 1102 via bus 1108. It should be understood that although not shown, other hardware and/or software components could be used in conjunction with computer system/server 1102. Examples, include, but are not limited to: microcode, device drivers, redundant processing units, external disk drive arrays, RAID systems, tape drives, and data archival storage systems, etc.

The terms "an embodiment", "embodiment", "embodiments", "the embodiment", "the embodiments", "one or more embodiments", "some embodiments", and "one embodiment" mean "one or more (but not all) embodiments of the present invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

Devices that are in communication with each other need not be in continuous communication with each other, unless expressly specified otherwise. In addition, devices that are in communication with each other may communicate directly or indirectly through one or more intermediaries.

A description of an embodiment with several components in communication with each other does not imply that all such components are required. On the contrary a variety of optional components are described to illustrate the wide variety of possible embodiments of the present invention.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the present invention need not include the device itself.

The foregoing description of various embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto. The above specification, examples and data provide a complete description of the manufacture and use of the composition of the invention. Since many embodiments of the invention can be made without departing from the spirit and scope of the invention, the invention resides in the claims herein after appended.

What is claimed is:

1. A computer program product for prioritizing information to present to at least one user operating at least one computing device, wherein the computer program product comprises a computer readable storage medium having program instructions embodied therewith, that when executed cause operations, the operations comprising:

providing user interaction information with natural language processing (NLP) items presented in documents for users to correct, wherein the NLP items are identified in the documents using a natural language processor, and wherein the user interaction information for the NLP items indicates user interaction frequencies with the NLP items for users that have interacted with the NLP items presented in the documents and context attribute values related to user interactions with the NLP items;

determining, using the natural language processor, NLP items in a selected document to present to a reviewing user, wherein the NLP items in the selected document have content to review to correct for errors;

determining a context attribute value for the selected document;

determining user interaction information for the NLP items in the selected document from users other than the reviewing user having the determined context attribute value;

calculating cumulative interaction frequencies for the NLP items in the selected document from user interaction frequencies in the determined user interaction information for the users that have interacted with the NLP items;

determining an order to present the NLP items in the selected document to present to the reviewing user to correct based on the cumulative interaction frequencies determined for the NLP items in the selected document; and transmitting, to a computing device of the reviewing user, the selected document with the determined NLP items presented in the determined order for the reviewing user to review and correct.

2. The computer program product of claim 1, wherein the operations further comprise:

receiving, from the computing device of the reviewing user, modifications to content for the determined NLP items in the selected document transmitted to the reviewing user;

modifying the content for the determined NLP items in the selected document with the modifications to the content; and saving the selected document having the modified content.

3. The computer program product of claim 1, wherein the operations further comprise:

processing the selected document to determine errors in content provided for the determined NLP items in the selected document, wherein the transmitted selected document is for the determined NLP items determined to have errors.

4. The computer program product of claim 1, wherein the user interactions with the determined NLP items comprises at least one of entering text for the determined NLP items, viewing the determined NLP items, and selecting the determined NLP items without entering text for the determined NLP items.

5. The computer program product of claim 1, wherein the determining the order of the determined NLP items in the selected document based on the cumulative interaction frequencies comprises:

assigning a priority to each of the determined NLP items based on the cumulative interaction frequencies for the determined NLP items; and determining the order in which to present the determined NLP items in the selected document according to priorities assigned to the determined NLP items to present the determined NLP items having a higher priority before the determined NLP items having a lower priority.

6. The computer program product of claim 1, wherein the operations further comprise:

determining a profile attribute value of the reviewing user from a plurality of profile attribute values, wherein the user interaction information is further determined from user interaction information generated from interactions by users having the determined profile attribute value; and assigning priority values to the determined NLP items based on the cumulative interaction frequencies with the determined NLP items by the users having the profile attribute value and the determined context attribute value, wherein the order of presenting the determined NLP items is determined according to the priority values assigned to the determined NLP items.

7. The computer program product of claim 1, wherein the user interaction information on the user interactions with the determined NLP items having the context attribute value are gathered from a plurality of users at a plurality of computing devices interacting with NLP items from multiple documents, and wherein the user interaction information used to determine priorities for the NLP items are gathered from the plurality of users.

8. The computer program product of claim 7, wherein the plurality of users are associated with a profile value of a plurality of profile values, wherein the user interaction information indicates the profile value of one of the plurality of users that interacted with an NLP item for which the user interaction information was generated, wherein the determining the user interaction information comprises determining interaction information having a profile value of the profile value of the reviewing user to receive the determined NLP items from the selected document.

9. The computer program product of claim 1, wherein the context attribute value comprises at least one of: user values related to user attributes of a user when interacting with the NLP item; a question subject attribute value indicating a subject of an interrogative sentence including the NLP item interacted with by the user; and an NLP item specific attribute value specific to a context of the determined NLP item in the selected document.

10. The computer program product of claim 9, wherein the user attributes include at least one of a location attribute comprising one of a plurality of location attribute values for different location descriptions of where the user was located when interacting with the NLP item, a time attribute comprising one of a plurality of time period values of when the user was interacting with the NLP item, and a user cohort value comprising one of a plurality of user cohort values of groups of users;

wherein the question subject attribute value indicates at least one of an age attribute having one of a plurality of age values of the subject, and at least one additional subject attribute relevant to the interrogative sentence including the NLP item; and wherein the NLP item specific attribute comprises an interrogative attribute having an interrogative attribute value comprising the interrogative sentence including the NLP item interacted with by the user.

11. The computer program product of claim 10, wherein the users comprise medical professionals, the subject of interrogative sentences including the NLP items comprises a patient, the NLP items are related to medical treatment of patients, the documents comprise patient medical records, wherein the location attribute values include a type of medical facility where the user is located, wherein the at least one additional subject attribute comprises at least one medical condition of the subject, and wherein the interrogative sentences including the NLP items concern gathering medical information related to the patients that are subjects of the interrogative sentences.

12. A system for prioritizing information to present to at least one user operating at least one computing device, comprising:

a processor; and a computer readable storage medium having program instructions embodied therewith, that when executed by the processor cause operations, the operations comprising:

providing user interaction information with natural language processing (NLP) items presented in documents for users to correct, wherein the NLP items are identified in the documents using a natural language processor, and wherein the user interaction information for the NLP items indicates user interaction frequencies with the NLP items for users that have interacted with the NLP items presented in the documents and context attribute values related to user interactions with the NLP items;

determining, using the natural language processor, NLP items in a selected document to present to a reviewing user, wherein the NLP items in the selected document have content to review to correct for errors;

determining a context attribute value for the selected document;

determining user interaction information for the NLP items in the selected document from users other than the reviewing user having the determined context attribute value;

calculating cumulative interaction frequencies for the NLP items in the selected document from user interaction frequencies in the determined user interaction information for the users that have interacted with the NLP items;

determining an order to present the NLP items in the selected document to present to the reviewing user to correct based on the cumulative interaction frequencies determined for the NLP items in the selected document; and transmitting, to a computing device of the reviewing user, the selected document with the determined NLP items presented in the determined order for the reviewing user to review and correct.

13. The system of claim 12, wherein the determining the order of the determined NLP items in the selected document based on the cumulative interaction frequencies comprises:

assigning a priority to each of the determined NLP items based on the cumulative interaction frequencies for the determined NLP items; and determining the order in which to present the determined NLP items in the selected document according to priorities assigned to the determined NLP items to present the determined NLP items having a higher priority before the determined NLP items having a lower priority.

14. The system of claim 12, wherein the operations further comprise:

determining a profile attribute value of the reviewing user from a plurality of profile attribute values, wherein the user interaction information is further determined from user interaction information generated from interactions by users having the determined profile attribute value; and assigning priority values to the determined NLP items based on the cumulative interaction frequencies with the determined NLP items by the users having the profile attribute value and the determined context attribute value, wherein the order of presenting the determined NLP items is determined according to the priority values assigned to the determined NLP items.

15. The system of claim 12, wherein the context attribute value comprises at least one of: user values related to user attributes of a user when interacting with the NLP item; a question subject attribute value indicating a subject of an interrogative sentence including the NLP item interacted with by the user; and an NLP item specific attribute value specific to a context of the determined NLP item in the selected document.

16. The system of claim 12, wherein the operations further comprise:

receiving, from the computing device of the reviewing user, modifications to content for the determined NLP items in the selected document transmitted to the reviewing user;

modifying the content for the determined NLP items in the selected document with the modifications to the content; and saving the selected document having the modified content.

17. The system of claim 12, wherein the operations further comprise:

processing the selected document to determine errors in content provided for the determined NLP items in the selected document, wherein the transmitted selected document is for the determined NLP items determined to have errors.

18. The system of claim 12, wherein the user interactions with the determined NLP items comprises at least one of entering text for the determined NLP items, viewing the determined NLP items, and selecting the determined NLP items without entering text for the determined NLP items.

19. The system of claim 12, wherein the user interaction information on the user interactions with the NLP items having the context attribute value are gathered from a plurality of users at a plurality of computing devices interacting with NLP items from multiple documents, and wherein the user interaction information used to determine priorities for the NLP items are gathered from the plurality of users.

20. The system of claim 19, wherein the plurality of users are associated with a profile value of a plurality of profile values, wherein the user interaction information indicates the profile value of one of the plurality of users that interacted with an NLP item for which the user interaction information was generated, wherein the determining the user interaction information comprises determining interaction information having a profile value of the profile value of the reviewing user to receive the determined NLP items from the selected document.

* * * * *